United States Patent
Huang (10) Patent No.: US 10,682,162 B2
(45) Date of Patent: Jun. 16, 2020

(54) SKULL FIXING DEVICE

(71) Applicant: OSSAWARE BIOTECH CO., LTD., Changhua County (TW)

(72) Inventor: Max Huang, Changhua County (TW)

(73) Assignee: OSSAWARE BIOTECH CO., LTD., Changhua County (TW)

( * ) Notice: Subject to any disclaimer, the term of this patent is extended or adjusted under 35 U.S.C. 154(b) by 641 days.

(21) Appl. No.: 15/489,736

(22) Filed: Apr. 18, 2017

(65) Prior Publication Data

US 2018/0296247 A1  Oct. 18, 2018

(51) Int. Cl.
*A61B 17/68* (2006.01)
*A61B 17/86* (2006.01)

(52) U.S. Cl.
CPC ........ *A61B 17/688* (2013.01); *A61B 17/8605* (2013.01); *A61B 17/8665* (2013.01)

(58) Field of Classification Search
CPC .............. A61B 17/688; A61B 17/8605; A61B 17/8665
See application file for complete search history.

(56) References Cited

U.S. PATENT DOCUMENTS

| | | | | |
|---|---|---|---|---|
| 5,707,373 A | * | 1/1998 | Sevrain | A61B 17/688 411/338 |
| 2008/0039837 A1 | * | 2/2008 | Gambale | A61B 17/688 606/60 |
| 2014/0257412 A1 | * | 9/2014 | Patty | A61B 17/8615 606/308 |

* cited by examiner

*Primary Examiner* — Kai H Weng
(74) *Attorney, Agent, or Firm* — Leong C. Lei (57) ABSTRACT

A skull fixing device includes at least a lower fastening member and a movable retainer assembly. The lower fastening member includes a thread rod having a first coupling section formed in an interior thereof. The movable retainer assembly includes at least an upper fastening member and a nut. The upper fastening member includes a sleeve section in which a first rotation section is formed. The nut is screwed to the threaded rod and has an upper end forming a first positioning section and has an outer surface forming a second rotation section mating the first rotation section. Also disclosed is a surgery tool that includes at least a outer barrel having a lower end forming a second positioning section engageable with the first positioning section and an inner guide rod having a lower end forming a second coupling section engageable with the first coupling section.

14 Claims, 13 Drawing Sheets

SKULL FIXING DEVICE

(a) TECHNICAL FIELD OF THE INVENTION

The present invention relates generally to a skull fixing device, and more particularly to a skull fixing device that allows for easy, effective, and efficient implantation and removal of the fixing device in a clinic operation.

(b) DESCRIPTION OF THE PRIOR ART

Fixing devices for skulls are known. For example Taiwan Patent Publication No. 1321463 discloses a fixing device for skulls, which comprises a sleeve, which comprises a tube, a flange formed on one end of the tube, a bottom plate mounted to an opposite end of the tube, and a through hole formed in the bottom plate; a bolt, which has a head and a body extending from the head and received through the through hole of the sleeve; and a nut, which is screwed to the body of the bolt and is located in the tube of the sleeve.

Such a known fixing device is effective in positioning a skull and offering protection to a patient's head, and is also repeatedly usable. However, the sleeve, the bolt, and the nut are separate parts and they must be held, in sequence, with a clamp device before they are implanted and properly positioned. Particularly, after the bolt is implanted, the clamp device must be first released to allow the skull to be returned to the original location, and then the clamp device is operated again to implant the sleeve and the nut. This causes certain inconvenience in a clinic operation, and in addition, after all these parts have been placed in position, an additional wrenching tool must be applied to engage a top slot formed in the nut for rotating the nut to screw and move down along the bolt and thus induce a clamping force between the sleeve and the bolt to securely fix the skull. This makes it necessary for a clamp tool in implanting and positioning all the parts and another tool for wrenching would later used for rotating and tightening. Both implantation and removal operations require the two tools and costs would be high and clinic operations become complicated and inconvenient.

In addition, the fixing device is structured by providing a plurality of slots in the top of the nut for engagement with corresponding projections of an implantation tool in order to rotate and drive the nut to screw to the bolt and to drive the sleeve to press down for fixing. However, the projection-slot engagement of the implantation tool with the nut is achieved only between a lower part of the implantation tool and a top circumferential portion of the nut, and thus, the engagement is generally not very secure and would readily lead to undesired separation between the implantation tool and the nut during screwing of the nut, making it necessary for re-positioning for engagement. The operation is very inconvenient.

Further, liquid accumulation often occurs inside the patient's head after the operation. The tissue fluid must be effectively and quickly drained in order to prevent excessive brain pressure and swelling. However, the known fixing device is generally not equipped with a drainage structure. Thus, surgeons must drill a hole at a neighboring site for insertion and installation of a drain tube. This increases the inconvenience of a surgery operation.

In view of the above, the present invention provides the present invention, which will be described hereinafter, to overcome such drawbacks of the prior art devices.

SUMMARY OF THE INVENTION

The primary objective of the present invention is to effectively simplify a component assembling operation to achieve convenience of easy and efficient completion of the component assembling operation.

Another objective of the present invention is to accomplish implantation and removal through the use of on single implantation tool with one hand handling one single component so as to effectively simplify an operation process so that the operations for both implantation and remove can be done easily, efficiently, and conveniently.

A further objective of the present invention is to provide a skull fixing device provides an additional function of fluid draining.

To achieve the above objectives, a technical solution adopted in the present invention comprises: providing a skull fixing device that comprises:

a lower fastening member and a movable retainer assembly, wherein the lower fastening member comprises a first base section, a threaded rod having an external thread, and a first coupling section arranged in an interior of the threaded rod; and the movable retainer assembly comprises at least an upper fastening member and a nut, wherein the upper fastening member comprises a second base section and a sleeve section; the sleeve section is provided in an interior thereof with a first rotation section; the nut is received in the sleeve section and comprises an internal thread engageable with the external thread of the threaded rod and is provided, on an upper end thereof, with a first positioning section; and the nut has an outside surface that is provided with a second rotation section rotatably coupled with the first rotation section of the upper fastening member such that the nut and the upper fastening member collectively form the removable retainer assembly.

The above skull fixing device further comprises an implantation tool, wherein the implantation tool comprises an inner guide rod and an outer barrel, wherein the inner guide rod has a lower end that is provided with a second coupling section combinable with the first coupling section of the threaded rod and an upper end that is provided with a third coupling section below a grip; the outer barrel comprises a guide hole through which the inner guide rod is receivable; the guide hole is provided, on an upper end of an interior thereof, with a fourth coupling section that is combinable with the third coupling section of the inner guide rod such that when the outer barrel and the inner guide rod are coupled and positioned through combination of the third coupling section and the fourth coupling section, the outer barrel and the second coupling section of the lower end of the inner guide rod comprises a spacing distance defined therebetween; and the outer barrel has a lower end to which a second positioning section engageable with the first positioning section of the nut is mounted.

In the above skull fixing device, the first coupling section in the interior of the threaded rod comprises an internal thread and the second coupling section of the guide rod that is combinable with the first coupling section comprises an external thread, and the third coupling section comprises an external thread that has a thread direction that is different from the second coupling section so that the second coupling section comprises a right-handed external thread, the third coupling section comprises a left-handed external thread, the fourth coupling section comprises a left-handed internal thread that is engageable with the left-handed external thread of the third coupling section.

In the above skull fixing device, the sleeve section comprises an annular sleeve having a cavity section having a bottom in which a through hole is formed and the first rotation section is formed as a retention slot by recessing an inner surface of the cavity section, and the second rotation section comprises an annular projection receivable in and movably engageable with the retention slot of the first rotation section.

In the above skull fixing device, the fixing device comprises a drain channel for installation of a drain tube.

In the above skull fixing device, the third coupling section comprises a coupling portion that has a non-circular shape and the fourth coupling section comprises a positioning trough that is formed through recessing a top end of the outer barrel and corresponding in shape to the third coupling section, and the third coupling section and the fourth coupling section have shapes that are identical and non-circular so that the third coupling section and the fourth coupling section are combinable in a manner of being in driving engagement with each other for movability in unison with each other.

As such, the upper fastening member and the nut of the present invention are rotatably combined together as a single movable retainer assembly to facilitate setting and positioning of the entire combination of movable retainer assembly and the outer barrel. The outer barrel is combinable with and positioned on an upper end of the inner guide rod, such that the movable retainer assembly is set to be spaced from an outer surface of a skull by a spacing distance to facilitate implantation and position restoration of the skull cover. The implantation tool comprises just one single piece of tool and the upper and lower ends of the inner guide rod are respectively provided with threads of opposite directions so that by holding and rotating one single component, the outer barrel, in one direction to move vertically, implantation and removal can be achieved thereby providing the advantages of an efficient and easy way of operation and improving the drawbacks of the prior art.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the de ailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
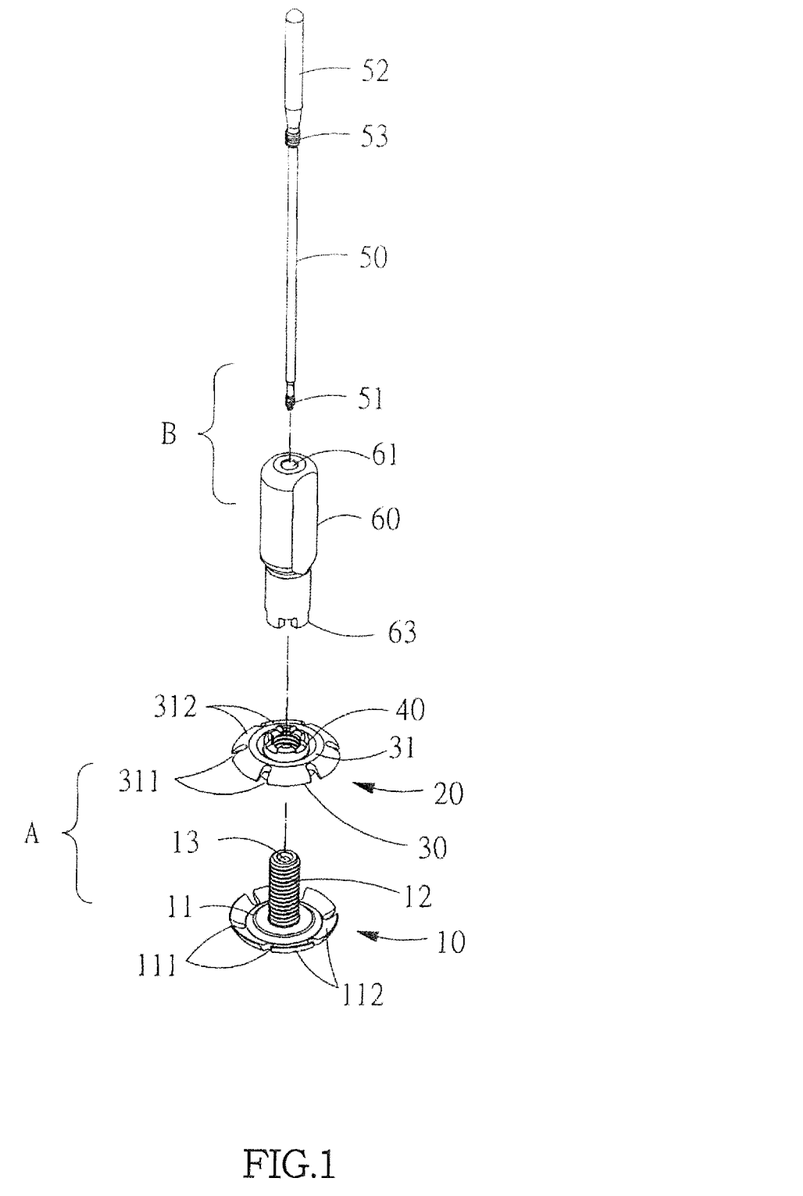
FIG. 1 is an exploded view of the present invention.
Figure 2:
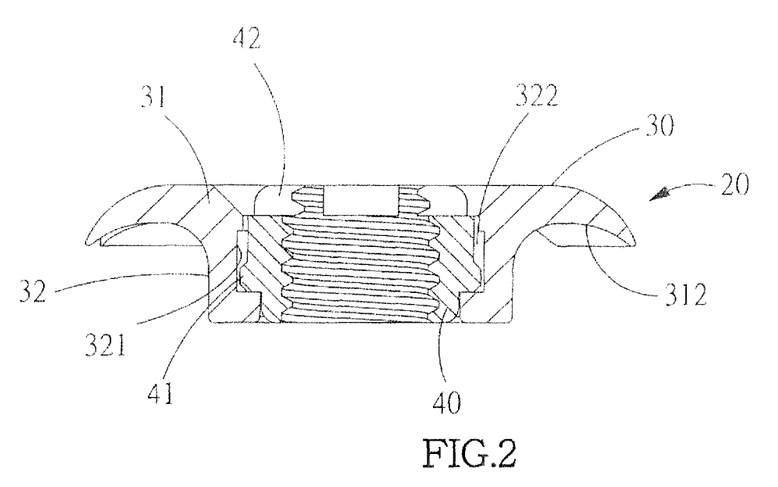
FIG. 2 is a cross-sectional view of a movable retainer assembly of the present invention.

As shown in FIGS. 1-4, the present invention provides a skull fixing device A, which comprises:

a lower fastening member 10, which comprises a first base section 11, a threaded rod 12 having an external thread, and a first coupling section 13 arranged in an interior of the threaded rod 12, wherein the first base section 11 is in the form of a plate or a disk having an outer circumference that is formed with a plurality of open slits 111 at intervals so as to form a plurality of first petal sections 112; the plurality of first petal sections 112 have a thickness that is gradually reduced toward and terminates at an outer circumferential edge for easy insertion into a skull 70 and a skull cover 72 for fixing them together; and the first coupling section 13 comprises an internal thread; and a movable retainer assembly 20, which comprises at least an upper fastening member 30 and a nut 40 that is threadingly engageable with the external thread of the threaded rod 12, wherein the upper fastening member 30 comprises a second base section 31 and a sleeve section 32, the sleeve section 32 being provided in an interior thereof with a first rotation section 321; the second base section 31 is in the form of a plate or a disk having an outer circumference that is formed with a plurality of open slits 311 at intervals to form a plurality of second petal sections 312, the plurality of second petal sections 312 having a thickness that is gradually reduced toward and terminates at an outer circumferential edge for easy insertion into the skull 70 and the skull cover 72 for fixing them together; the sleeve section 32 comprises an annular sleeve that comprises a cavity section 322 having a bottom in which a through hole is formed, the first rotation section 321 being formed as a retention slot by recessing an inner surface of the cavity section 322; the nut 40 is received in the cavity section 322 of the sleeve section 32 and the nut 40 comprises an internal thread that is threadingly engageable with the external thread of the threaded rod 12 and is also provided, on an upper end thereof, with a first positioning section 42, where the first positioning section 42 is engageable with and combinable with an implantation tool B, and preferably, the first positioning section 42 comprises a corrugated arrangement circumferentially formed on a circumference of an upper end of the nut 12 or comprises at least two pit structures (not shown) formed by recessing an end surface, the nut 40 having an outer surface that is provided with a second rotation section 41 that is rotatably combinable with the first rotation section 321 of the upper fastening member 30, wherein in the instant embodiment, the second rotation section 41 comprises an annular projection receivable in and movably engageable with the retention slot of the first rotation section 321 so that the nut 40 and the upper fastening member 30 collectively form the movable retainer assembly, as shown in FIG. 2.

Figure 3:
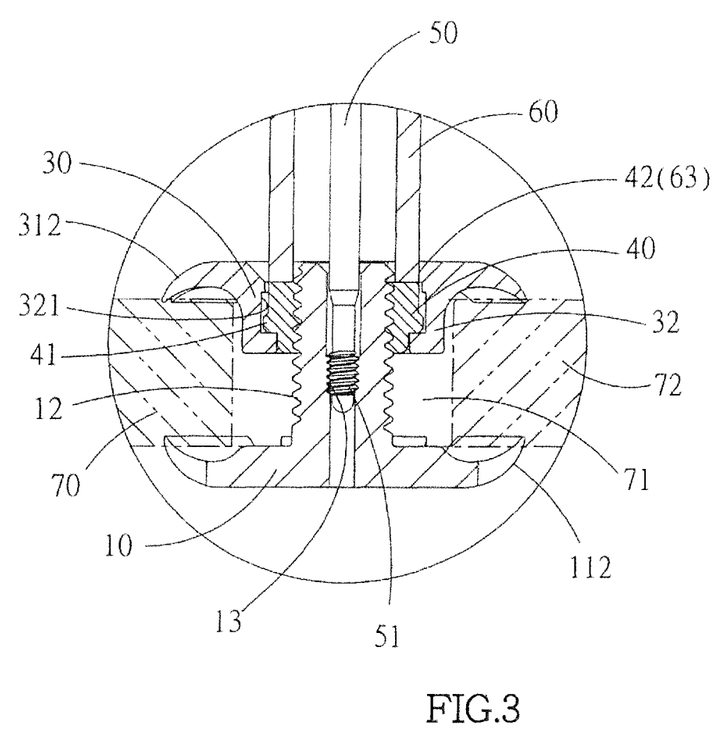
FIG. 3 is a schematic view illustrating a combination of a fixing device and an implantation tool according to the present invention.

The present invention further comprises an implantation tool B, which comprises an inner guide rod 50 and an outer barrel 60. The inner guide rod 50 has a lower end to which a second coupling section 51 is formed and is combinable with the first coupling section 13 provided in the interior of the threaded rod 12 the fixing device A, wherein the second coupling section 51 comprises an external thread that is threadingly engageable with the internal thread of the first coupling section 13; or alternatively, the first coupling section 13 comprises a positioning block projecting from the lower end of the inner guide rod 50 and the second coupling section 51 comprises a coupling hole that is provided on the threaded rod 12 and comprises an L-shaped positioning slot to receive the positioning block to insert and rotate therein to achieve positioning (not illustrated). The inner guide rod 50 has an upper end that is provided with a grip section 52 and a third coupling section 53 is arranged below the grip section 52. Preferably, the third coupling section 53 comprises an external thread. The outer barrel 60 comprises a guide hole 61 that receives the inner guide rod 50 to extend therethrough. The guide hole 61 is provided, on an upper end of an interior thereof, with a fourth coupling section 62 that is combinable with the third coupling section 53 of the inner guide rod 50 so as to have the outer barrel 60 coupled to and positioned with respect to the inner guide rod 50 in such a way that the outer barrel 60 and the second coupling section 51 of the inner guide rod 50 comprises a spacing distance X defined therebetween. The fourth coupling section 62 comprises an internal thread corresponding to and threadingly engageable with the external thread of the third coupling section 53. The thread direction of the second coupling section 51 is different from the thread direction of the third coupling section 53 and the fourth coupling section 62, and preferably, the second coupling section 51 comprises right-handed thread, while the third coupling section 53 and the fourth coupling section 62 comprise left-handed threads. The outer barrel 60 has a lower end on which a second positioning section 63 is provided. The second positioning section 63 comprises a corrugated arrangement formed on a circumference of a lower end of the outer barrel 60 to correspond to and mate the corrugated arranged of the first positioning section 42 so as to be connected with and driving the nut 40 to move in unison therewith; or alternatively, the outer barrel 60 is provided, on a lower end thereof, with two bumps corresponding to and mating the two pits formed in the first positioning section 42 for driving the nut 40 to move in unison therewith (not illustrated).

Figure 10:
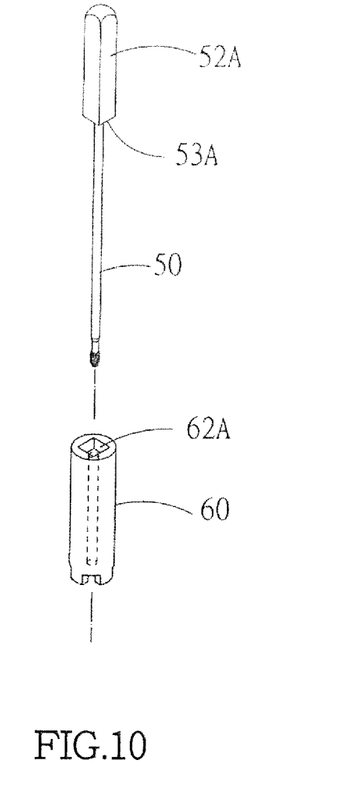
FIG. 10 is a schematic view illustrating another embodiment of third and fourth coupling sections according to the present invention.
Figure 11:
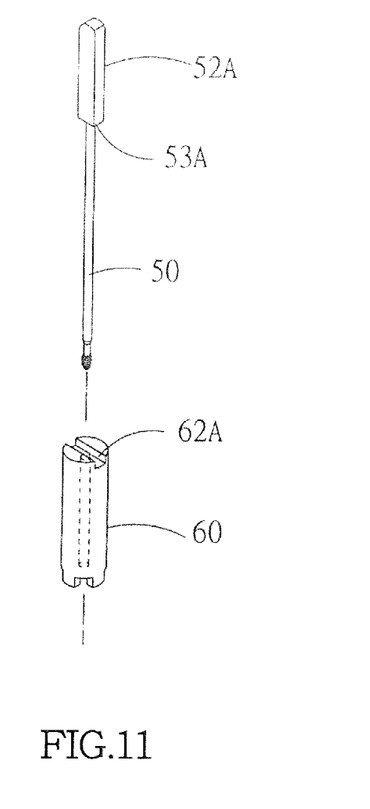
FIG. 11 is a schematic view illustrating a further embodiment of third and fourth coupling sections according to the present invention.

Referring to FIGS. 10 and 11, schematic views are given to illustrate another embodiment of the third coupling section and the fourth coupling section. In the instant embodiment, the third coupling section 53A of the inner guide rod 50 may comprises a coupling section that is not a regular circular shape and the fourth coupling section 62A of the outer barrel 60 comprises a positioning slot formed in a top end of the outer barrel 60 and corresponding, in shape, to the third coupling section 53A, such as a linear slot or a rectangular slot as shown in the drawings. In other words, the third coupling section 53A and the fourth coupling section 62A comprise identical shapes that are not regular circle, so that the third coupling section 53A and the fourth coupling section 62A can mate and couple with each other in a manner of being movable in unison with each other. Further, the grip section 52A may have the same shape as that of the third coupling section so that the third coupling section 53A may be formed by directly extending the grip section 52A.

Figure 4:
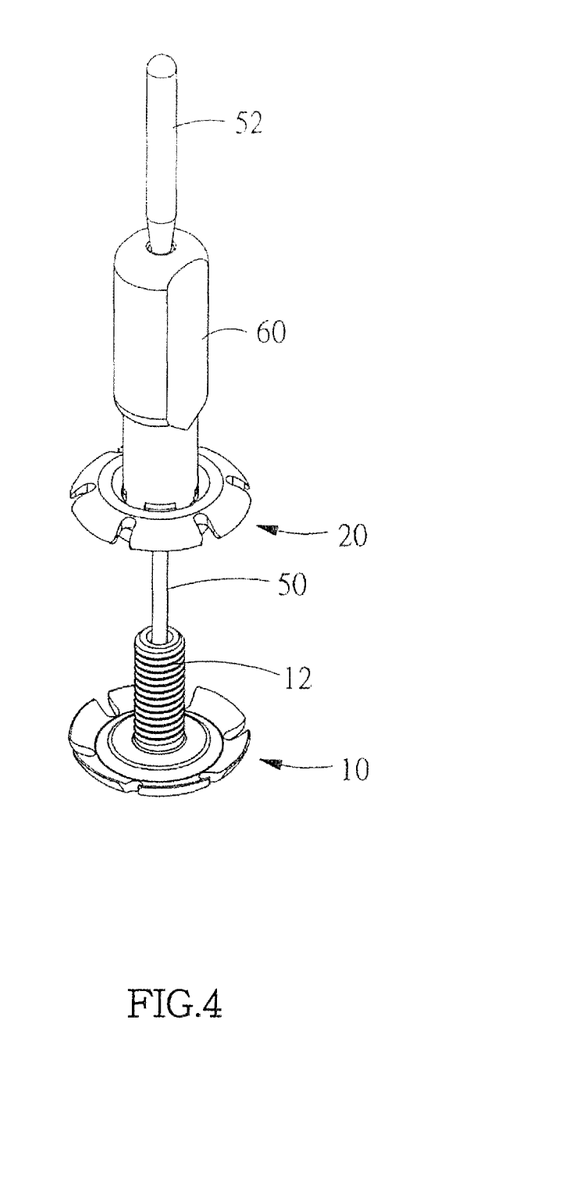
FIG. 4 is a perspective view showing the fixing device and the implantation tool of the present invention combined together.
Figure 5:
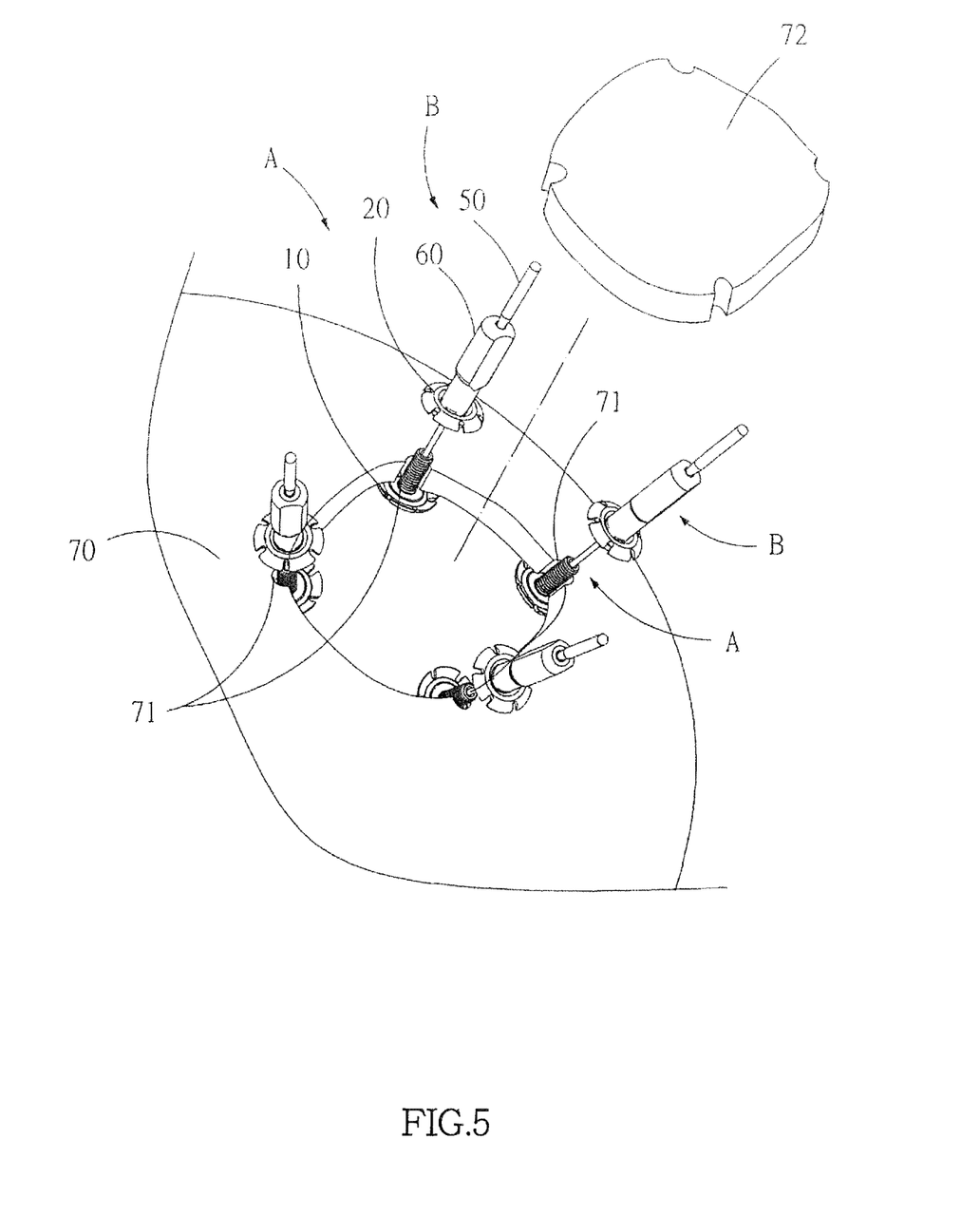
FIG. 5 is a schematic view illustrating an operation of implanting the combination of FIG. 4 in a drilled hole of a skull.
Figure 6:
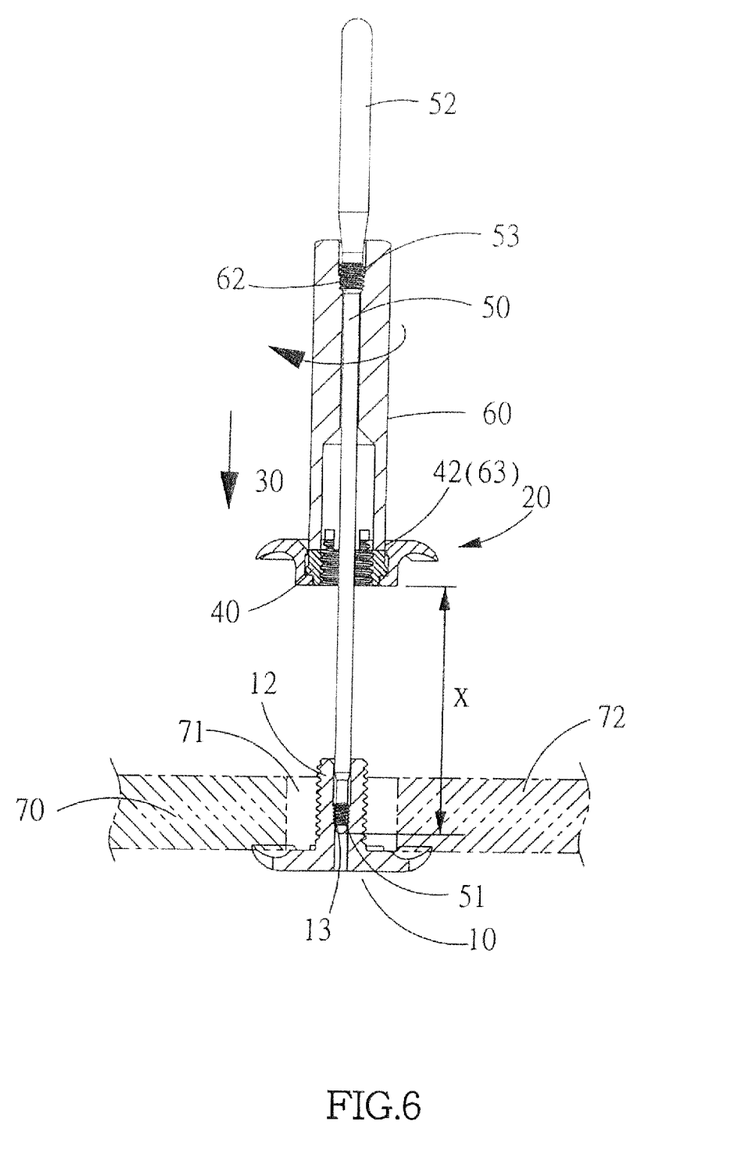
FIG. 6 is a schematic view illustrating implantation and position restoration of a skull cover of FIG. 5 through rotation and downward movement of an outer barrel according to the present invention.
Figure 7:
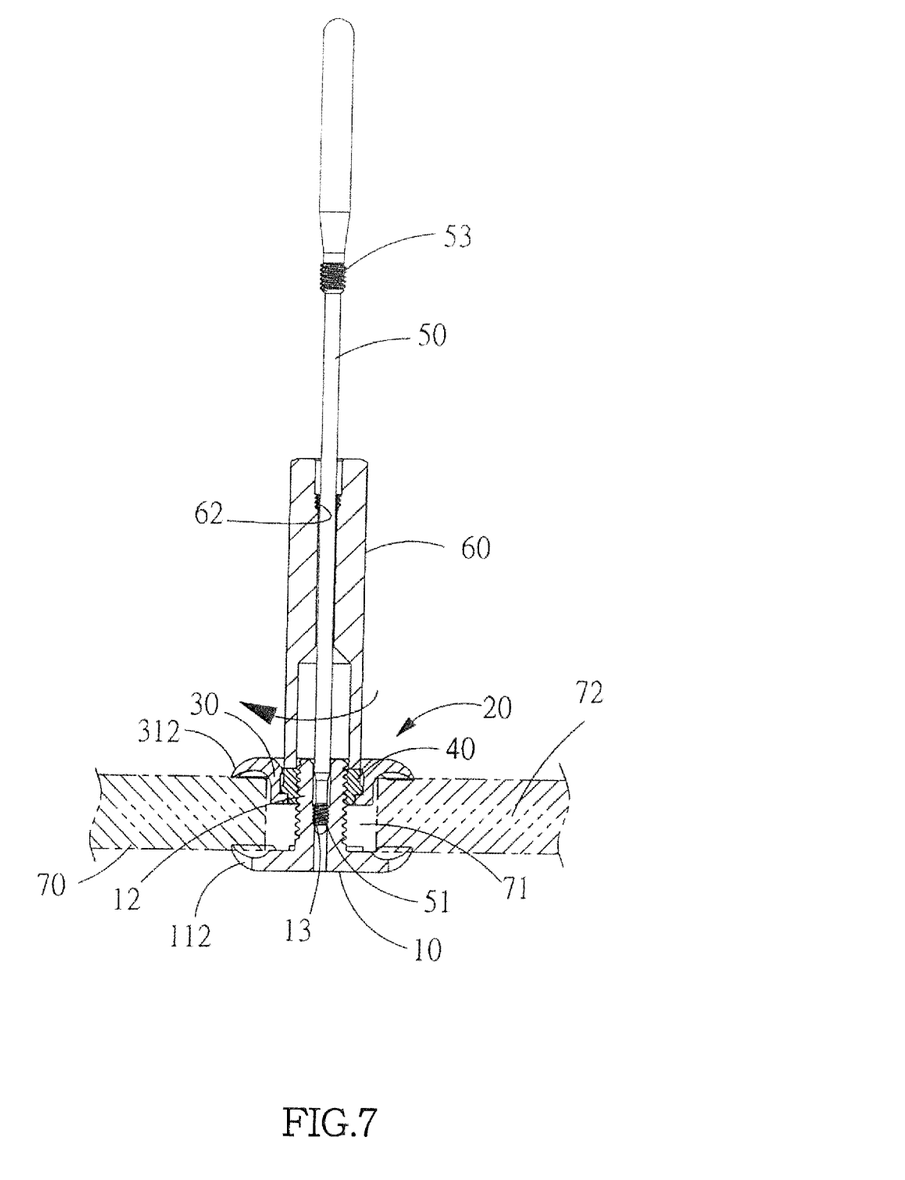
FIG. 7 is a schematic view illustrating the outer barrel of FIG. 6 is further continuously rotated to drive a nut and an upper fastening member to move downward to achieve securely clamping and fixing according to the present invention.
Figure 8:
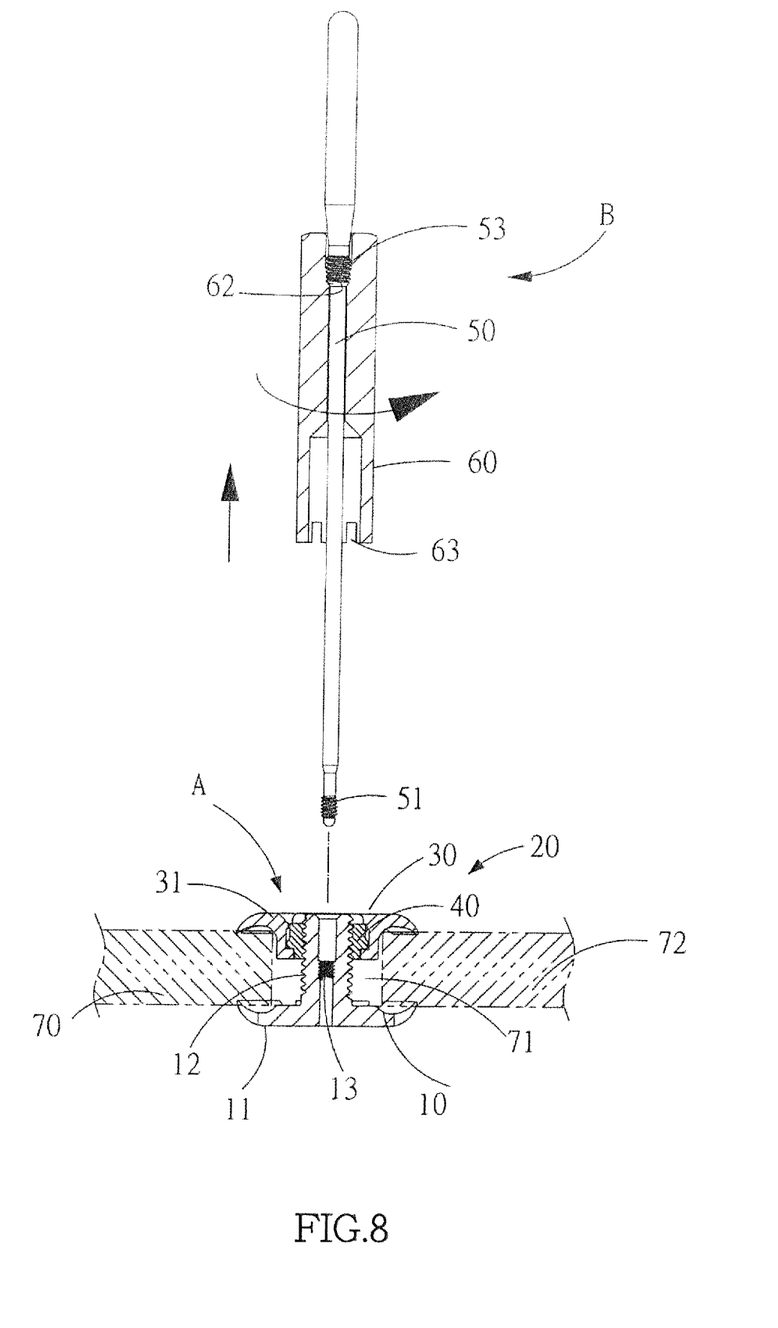
FIG. 8 is a schematic view illustrating the outer barrel of FIG. 7 moved upward to engage with an inner guide rod and further rotated to have the inner guide rod removed out of a threaded rod according to the present invention.
Figure 9:
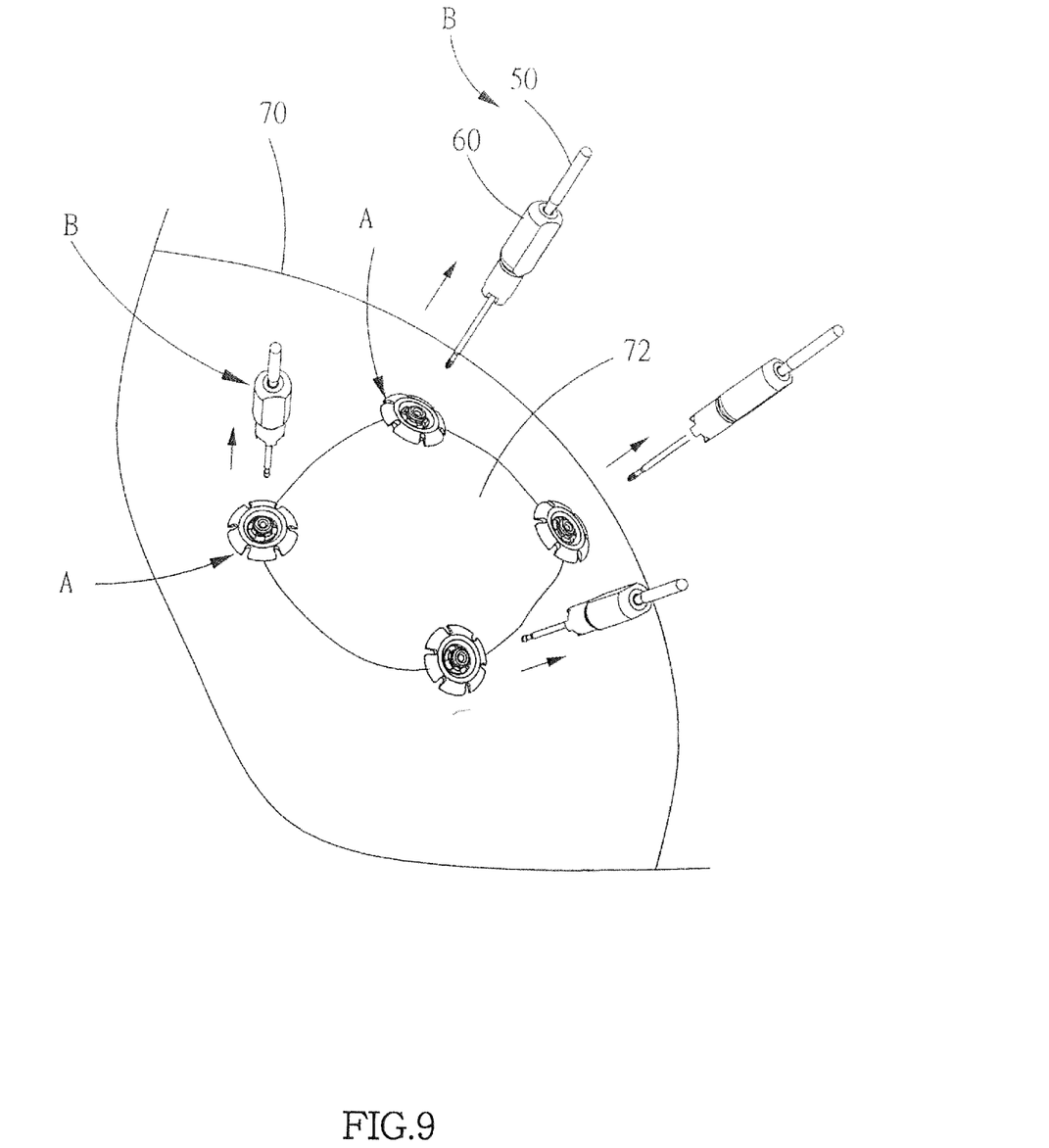
FIG. 9 is a perspective schematic view illustrating the implantation tool of FIG. 8 is completely removed according to the present invention.

Referring to FIGS. 4-9, schematic views are given to demonstrate assembling of the fixing device A and the implantation tool B and an implantation operation conducted therewith according to the present invention. In the instant embodiment, as shown in FIG. 4, it only needs to penetrate the inner guide rod 50 through the outer barrel 60 and the movable retainer assembly 20 to have the second coupling section 51 on the lower end thereof screwed to the first coupling section 13 provided in the interior of the threaded rod 12 and the fourth coupling section 62 provided on the upper end of the outer barrel 60 screwed to the third coupling section 53 provided on the upper end of the inner guide rod 50 to achieve positioning. The movable retainer assembly 20 is coupled through engagement between the first positioning section 42 provided on the upper end of the nut 40 and the second positioning section 63 provided on the lower end of the outer barrel 60 such that the fixing device A and the implantation tool B are combined with and positioned with respect to each other to form a combined assembly. As shown in FIG. 5, the fixing device A and the implantation tool B can be placed into a drilled hole 71 formed in skull 70 at the same time in an easy and convenient way. Further, as shown in FIG. 6, the outer barrel 60 and the second coupling section 51 of the inner guide rod 50 comprise a spacing distance X defined therebetween such that when the outer barrel 60 is combined with the movable retainer assembly 20, the movable retainer assembly 20 is arranged in a manner of being spaced from an outer surface of the skull 70 by a distance to allow for easy setting and restoration of position of the skull cover 72. As shown in FIGS. 6 and 7, after the skull cover 72 is set for closure, the outer barrel 60 is rotated and thus moved downward, where driving engagement between the second positioning section 63 provided on the lower end thereof and the first positioning section 42 of the nut 40 allows the outer barrel 60 that is being rotated to drive the nut 60 and the threaded rod 12 to screw with each other and move downward thereby driving and tightening the upper fastening member 30 and the lower fastening member 10 to generate a clamping force for effectively and securely clamping and fixing the skull cover 72 in position on the skull 70. As shown in FIG. 8, the outer barrel 60 may then be moved upward through reversed rotation so that the fourth coupling section 62 and the third coupling section 53 of the inner guide rod 50 engage with each other and through further and continuous rotation, the second coupling section 51 provided on the lower end of the inner guide rod 50 is screwed out of and thus detached from the inner threaded hole of the first coupling section 13 of the threaded rod 12 allow the implantation tool B to be quickly removed from the fixing device A, as shown in FIG. 9. On the other hand, to remove the fixing device A or the skull cover 72, it only needs to conduct the operation in an opposite way to remove the fixing device A from the skull 70. The present invention is easy and convenient in operation for both implantation and removal.

The skull fixing device A and the implantation tool B according to the present invention, when compared to the prior art, provide the following advantages:

(1) The nut 40 and the upper fastening member 30 of the present invention are combined to each other in a rotatable manner to form a movable retainer assembly 20. This simplifies an assembly process of parts. Further, the fixing device A and the implantation tool B are combined, in advance, as a combined assembly so that, without the use of any tool, the entire combined assembly of the fixing device A and the implantation tool B can be implanted together so as to make an implantation operation easy and efficient. The drawback of the prior art of being inconvenient in use, where clamping tools are necessary for individually picking, clamping and implanting parts of a fixing device one by one.

(2) The outer barrel 60 of present invention, when screwed to and position with respect to the upper end of the inner guide rod 50, is such that the outer barrel 60 and the second coupling section 51 of the inner guide rod 50 comprise a spacing distance X formed therebetween and the nut 40 and the upper fastening member 30 are rotatably combined to form a movable retainer assembly 20, so that the movable retainer assembly 20, in the entirety thereof, can be coupled to and positioned with respect to the outer barrel 60 such that the spacing distance X provides a sufficient space to allow the movable retainer assembly 20 and the outer surface of the skull 70 to space from each other by a distance for easy insertion and restoration of position of the skull cover 72.

(3) The second positioning section 51 and third positioning section 53 provided on the lower end and the upper end of the inner guide rod 50 of the present invention are provided with threads in opposite directions so that to fasten and tighten, manual rotation and movement of one signal outer barrel 60 would allow the upper fastening member 30 and the lower fastening member 10 to press against the skull cover 72 and the skull 70 for securely clamping and positioning. Further, to remove the implantation tool B, it only needs to move the outer barrel 60 upward through opposite rotation to be thus removed from the fixing device A. The present invention allows for holding, with one single hand, one single component, the outer barrel 60, to conduct an operation to achieve ease and convenience of fast and smooth fastening and tightening the fixing device A and quick removal of the implantation tool B. Further, to remove the fixing device A, it only needs to operate in an opposite way. Thus, both implantation and removal can be achieved with the present invention by using one implantation tool with one hand to hold one signal component, so that clinic operations are made efficient and easy. The drawbacks of the prior art of being complicated and inconvenient in operation where two different implantation tools must be used respectively for clamping and fastening.

(4) In the present invention, in addition to the second positioning section 63 provided on the lower end of the outer barrel 60 for mating the first positioning section 42 of the nut 40, the outer barrel 60 is provided with the guide hole 61 that is fit over the inner guide rod 50 so as to have additional support with the inner guide rod 60 to enhance rotation stability of the outer barrel 60 without any concern of undesired detachment and the inconvenience of re-engaging the outer barrel 60 and the nut 40 due to undesired detachment therebetween can be prevented.

(5) The present invention uses the upper fastening member to cover the drilled hole 71 and tightening can be achieved by rotating the nut 40 for screwing with the threaded rod 12 so that damage of outside surfaces of the skull 70 and the skull cover 72 due to rotation of the upper fastening member 30 can be prevented thereby achieving positioning of the skull cover without hurting the patient's head, and allowing for repeated use.

Figure 12:
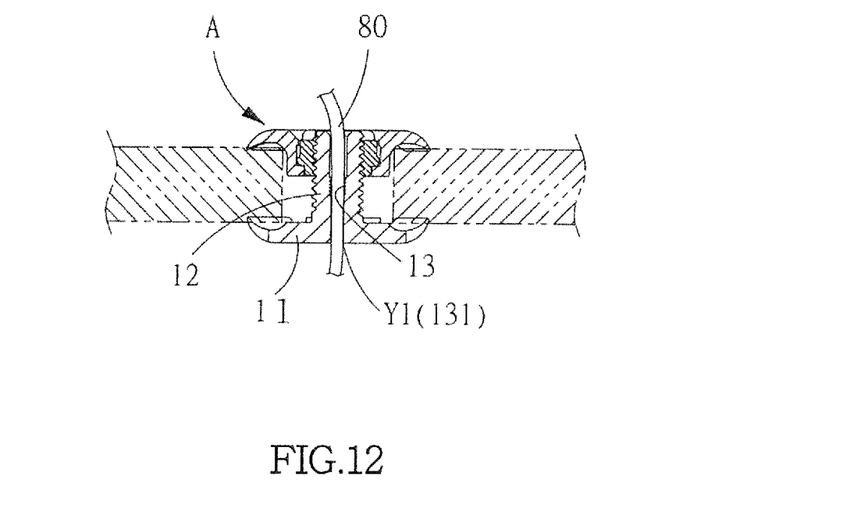
FIG. 12 is a schematic view illustrating the present invention in combination with a drain tube.

Further referring to FIG. 12, the fixing device A of the present invention is further provided with drain channel Y1. The drain channel Y1 is formed by extending from the internal thread of the first coupling section 13 to penetrate through the first base section 11 to form a through hole 131, which allows a drain tube 80 to insert therethrough for drain tissue fluid inside the brain thereby preventing excessive pressure and swelling of the brain due to accumulation of fluid.

Figure 13:
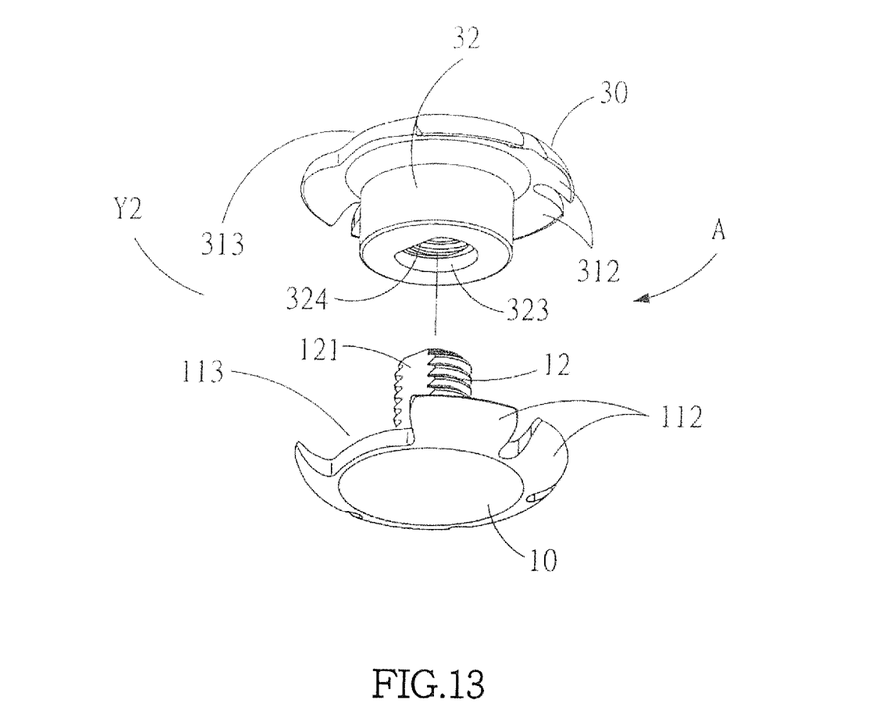
FIG. 13 is a schematic view illustrating another embodiment of combination of an upper fastening member and a lower fastening member according to the present invention.
Figure 14:
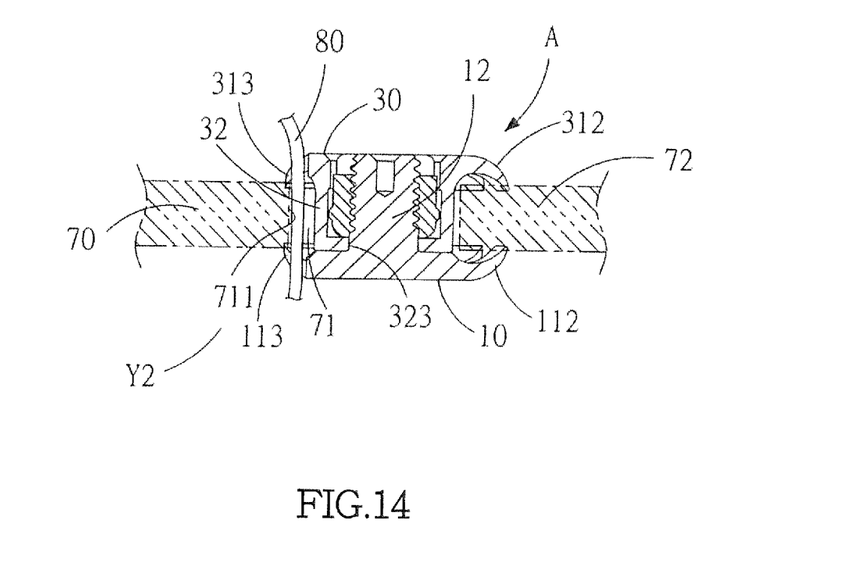
FIG. 14 is a schematic view illustrating the present invention as shown in FIG. 13 combined with a drain tube according to the present invention.

As shown in FIGS. 13 and 14, another embodiment that the fixing device A comprises a drain channel is illustrated. The fixing device A can be mounted in a drilled hole 71 in the skull 70 and the drain channel Y2 is formed in such a way that the plurality of first petals 312 of the upper fastening member 30 and the plurality of second petals 112 of the lower fastening member 10 are processed to have at least one petal of each of them corresponding to each other cut and removed to form a first notch 313 and a second notch 113. The sleeve section 32 of the upper fastening member 30 is formed with a through hole 323 that comprises an internal cut surface 324 and the threaded rod 12 of the lower fastening member 10 is provided with an external cut surface 121 corresponding to the internal cut surface 324 so that when the threaded rod 12 is fit into the through hole 323, the first notch 313 and the second notch 113 are set to correspond to each other. Further, the drilled hole 71 of the skull 70 is provided with an aperture 711 extending therethrough and corresponding to and in communication with the first notch 313 and the second notch 113 to receive a drain tube 80 to extend, vertically, through the first notch 313, the aperture 711, and the second notch 113 for insertion to drain brain tissue fluid to prevent excessive pressure and swelling of the brain due to accumulation of fluid.

Figure 15:
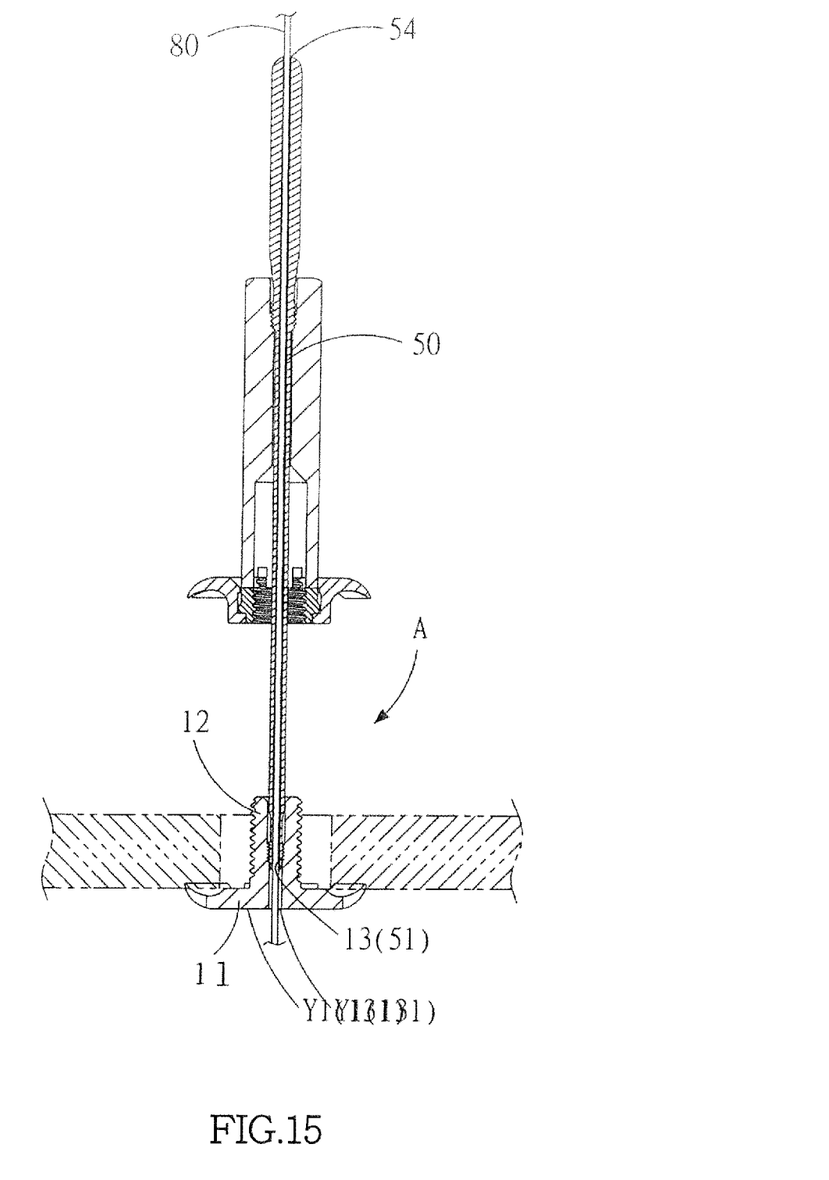
FIG. 15 is a schematic view illustrating a drain tube inserted through an inner guide rod according to the present invention.

As shown in FIG. 15, the present invention further comprises a hollow passage 54 formed in a center of and extending through the inner guide rod 50 and the fixing device A is provided with a drain channel Y1, similar to the previous cases. The drain channel Y1 extends from the internal thread of the first coupling section 13 to and through the first base section 11 to form a through hole 131, so that when the external thread of the second coupling section 51 of the inner guide rod 50 threadingly engages the internal thread of the first coupling section 13 of the threaded rod 12, the hollow passage 54 and the drain channel Y1 correspond to and communicate with each other to allow a drain tube 80 to insert through the hollow passage 54 of the inner guide rod 50 for draining brain tissue fluid to prevent excessive pressure and swelling of the brain due to accumulation of fluid.

Figure 16:
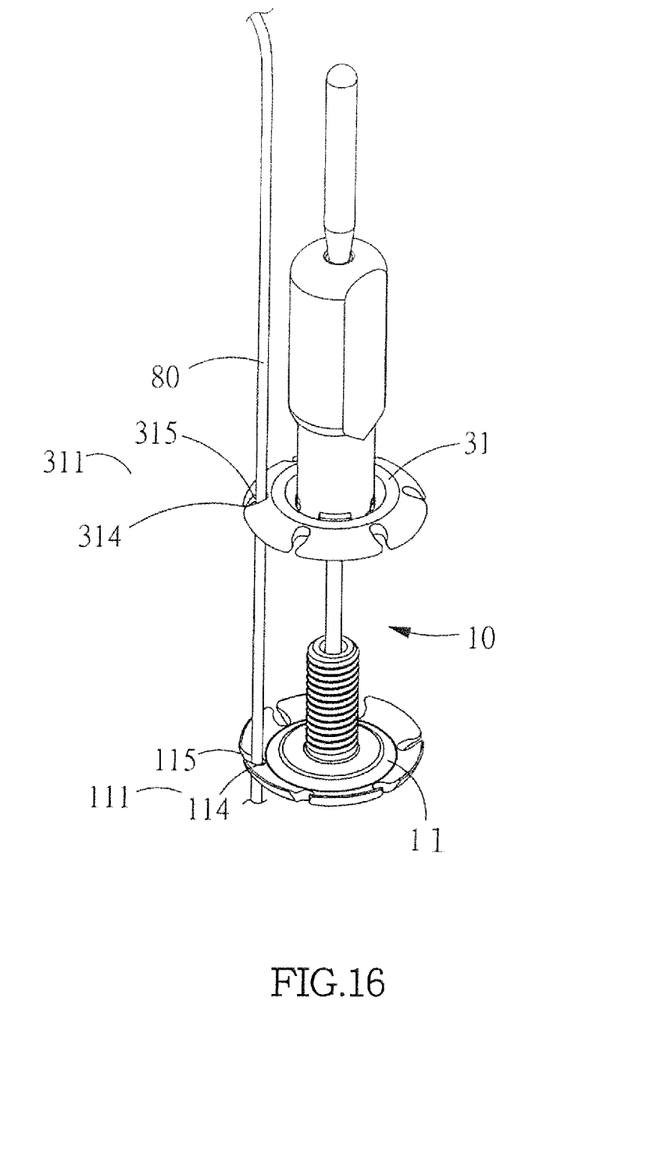
FIG. 16 is a perspective view showing a drain tube being received through and constrained in position by open slits according to the present invention.
Figure 17:
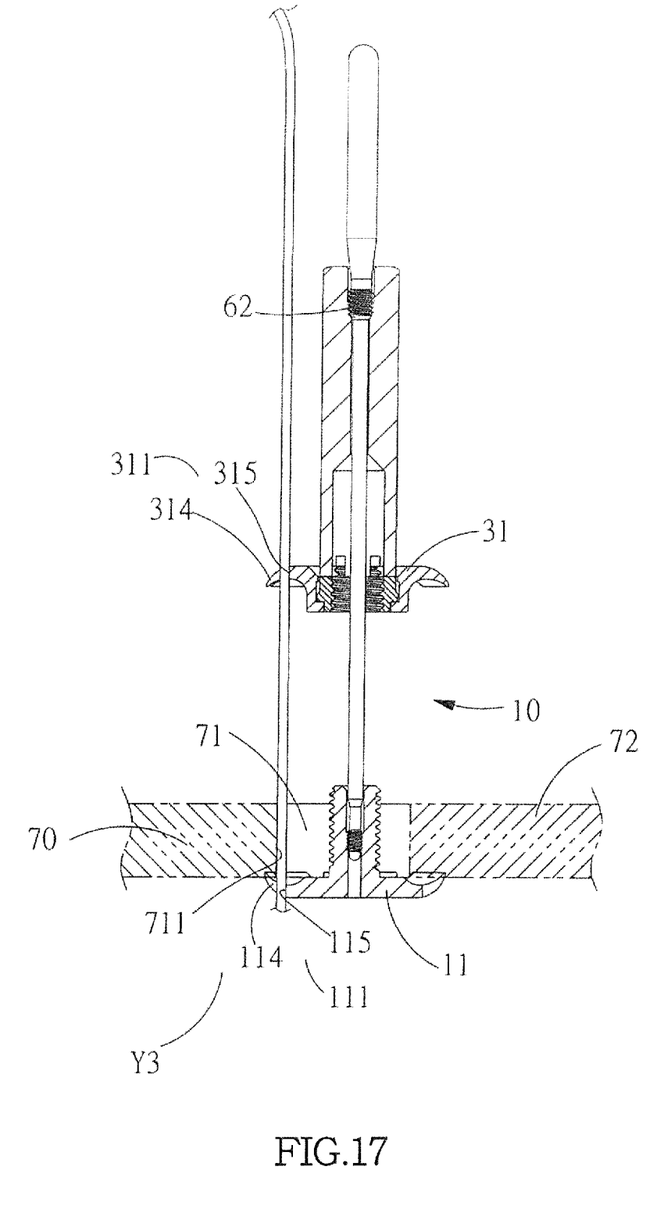
FIG. 17 is a schematic plan view of FIG. 16 according to the present invention.

As shown in FIGS. 16 and 17, the fixing device A is mounted at a drilled hole 71 of a skull 70 and the fixing device A comprises a drain channel Y3. The drain channel Y3 is such that the open slits 111, 311 of the first base section 11 and the second base section 31 are arranged to align with each other in a vertical direction to receive a drain tube 80 to extend therethrough. An aperture 711 is formed in the drilled hole 71 and the skull 70 corresponding to the open slits 111, 311 that correspond to each other in the vertical direction so as to allow a drain tube arranged between two open slits 111, 311 to be received through the aperture 711, whereby brain tissue fluid can be drained through the drain tube 80 to prevent excessive pressure and swelling of the brain due to accumulation of fluid. Further, the open slits 111, 311 are made in the form of a keyway, comprising an opening 114, 314 that is smaller than tube diameter of the drain tube and a position-constraining hole 115, 315 that is greater than the tube diameter of the drain tube to allow the drain tube 80 to be received and positioned therein.

In summary, the skull fixing device and the implantation tool according to the present invention are combinable, through the upper fastening member and the nut, to form a movable retainer assembly, and the implantation tool comprises just one single piece of tool. The upper and lower ends of the inner guide rod are respectively provided with threads of opposite directions so that by holding and rotating one single component, the outer barrel, in one direction to move vertically, implantation and removal can be achieved thereby providing the advantages of an efficient and easy way of operation.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A skull fixing device, comprising: a lower fastening member, which comprises a first base section, a threaded rod having an external thread, and a first coupling section arranged in an interior of the threaded rod; and a movable retainer assembly, which comprises an upper fastening member and a nut, the upper fastening member comprising a second base section and a sleeve section, the sleeve section being provided in an interior thereof with a first rotation section, the nut being received in the sleeve section and comprising an internal thread engageable with the external thread of the threaded rod and being provided, on an upper end thereof, with a first positioning section, the nut having an outside surface that is provided with a second rotation section rotatably coupled with the first rotation section of the upper fastening member such that the nut and the upper fastening member collectively form the removable retainer assembly.

2. The skull fixing device according to claim 1, wherein the fixing device comprises at least one drain channel for installation of a drain tube.

3. The skull fixing device according to claim 1 further comprising an implantation tool, wherein the implantation tool comprises an inner guide rod and an outer barrel, the inner guide rod having a lower end that is provided with a second coupling section combinable with the first coupling section of the threaded rod and an upper end that is provided with a third coupling section below a grip, the outer barrel comprising a guide hole through which the inner guide rod is receivable, the guide hole being provided, on an upper end of an interior thereof, with a fourth coupling section that is combinable with the third coupling section of the inner guide rod such that when the outer barrel and the inner guide rod are coupled and positioned through combination of the third coupling section and the fourth coupling section, the outer barrel and the second coupling section of the lower end of the inner guide rod comprises a spacing distance defined therebetween, the outer barrel having a lower end to which a second positioning section engageable with the first positioning section of the nut is mounted.

4. The skull fixing device according to claim 2 further comprising an implantation tool, wherein the implantation tool comprises a inner guide rod and an outer barrel, the inner guide rod having a lower end that is provided with a second coupling section combinable with the first coupling section of the threaded rod and an upper end that is provided with a third coupling section below a grip, the outer barrel comprising a guide hole through which the inner guide rod is receivable, the guide hole being provided, on an upper end of an interior thereof, with a fourth coupling section that is combinable with the third coupling section of the inner guide rod such that when the outer barrel and the inner guide rod are coupled and positioned through combination of the third coupling section and the fourth coupling section, the outer barrel and the second coupling section of the lower end of the inner guide rod comprises a spacing distance defined therebetween, the outer barrel having a lower end to which a second positioning section engageable with the first positioning section of the nut is mounted.

5. The skull fixing device according to claim 4, wherein the first coupling section in the interior of the threaded rod comprises an internal thread and the second coupling section of the guide rod that is combinable with the first coupling section comprises an external thread, the third coupling section comprising an external thread that has a thread direction that is different from the second coupling section so that the second coupling section comprises a right-handed external thread, the third coupling section comprises a left-handed external thread, the fourth coupling section comprises a left-handed internal thread that is engageable with the left-handed external thread of the third coupling section.

6. The skull fixing device according to claim 4, wherein the first coupling section in the interior of the threaded rod comprises an internal thread and the second coupling section of the guide rod that is combinable with the first coupling section comprises an external thread, the third coupling section comprising a coupling portion that has a non-circular shape, the fourth coupling section comprising a positioning trough that is formed through recessing a top end of the outer barrel and corresponding in shape to the third coupling section, the third coupling section and the fourth coupling section having shapes that are identical and non-circular so that the third coupling section and the fourth coupling section are combinable in a manner of being in driving engagement with each other for movability in unison with each other.

7. The skull fixing device according to claim 1, wherein the sleeve section comprises an annular sleeve having a cavity section having a bottom in which a through hole is formed, the first rotation section being formed as a retention slot by recessing an inner surface of the cavity section, the second rotation section comprising an annular projection receivable in and movably engageable with the retention slot of the first rotation section.

8. The skull fixing device according to claim 4, wherein the first positioning section comprises a corrugated arrangement circumferentially formed on a circumference of an upper end of the nut and the second positioning section comprises a corrugated arrangement formed on a circumference of a lower end of the outer barrel and engageable with the corrugated arrangement of the first positioning section.

9. The skull fixing device according to claim 1, wherein the first base section and the second base section each comprises a plate or a disk having an outer circumference that is formed with a plurality of open slits at intervals to form a plurality of first petal sections and a plurality of second petal sections, respectively, the plurality of first petal sections and the plurality of second petal sections having a thickness that is gradually reduced toward and terminates at an outer circumferential edge.

10. The skull fixing device according to claim 2, wherein the first coupling section in the interior of the threaded rod comprises an internal thread and the drain channel extending from the internal thread of the first coupling section through the threaded rod and the first base section to form a through hole, for receiving insertion and installation of the drain tube for fluid drainage.

11. The skull fixing device according to claim 4, wherein the first coupling section in the interior of the threaded rod comprises an internal thread, the second coupling section of the guide rod comprising an external thread engageable with the first coupling section, the drain channel extending from the internal thread of the first coupling section through the threaded rod and the first base section to form a through hole.

12. The skull fixing device according to claim 11, wherein the inner guide rod is formed in a center thereof with a hollow passage in communication with a through hole of the drain channel to allow the drain tube to extend through the hollow passage and the through hole of the drain channel into a brain.

13. The skull fixing device according to claim 9, wherein the fixing device is positionable in a drilled hole in a skull and the drain channel is formed of a first notch and a second notch formed by respectively removing one of the plurality of first petal sections and one of the plurality of second petal sections that correspond to each other, in combination with a through hole formed in a bottom of the sleeve section of the upper fastening member and having an internal cut surface and an external cut surface formed on the threaded rod of the lower fastening member such that the threaded rod is receivable in the through hole to have the first notch and the second notch corresponding in position to each other, an aperture being formed in the drilled hole of the skull and corresponding to the first notch and the second notch such that when the fixing device clamping and fixing the skull and a skull cover together, the drain tube is extendable through the first notch, the aperture, and the second notch for draining brain tissue fluid to prevent excessive pressure and swelling of the brain due to accumulation of fluid.

14. The skull fixing device according to claim 9, wherein, the fixing device is positionable in a dilled hole of a skull, the drain channel being formed of the open slits of the first base section and the second base section in aligned with each other in a vertical direction to receive the drain tube therein, an aperture being formed in the drilled hole of the skull and corresponding to the open slits that are in alignment with each other in the vertical direction so that the drain tube that is retained between two of open slits is receivable and positionable in the aperture.

\* \* \* \* \*